United States Patent [19]

Miller et al.

[11] Patent Number: 4,898,729

[45] Date of Patent: Feb. 6, 1990

[54] TREATMENT OF HYPERTENSION, COMPOUNDS AND COMPOSITIONS FOR ANTIHYPERTENSION AND DIURESIS

[75] Inventors: Ronald B. Miller, Harpenden, England; Alfred Halpern, Great Neck, N.Y.; Stewart Leslie, Cambridge, England; Peter Hofer, Liestal, Switzerland

[73] Assignee: Euroceltique, S.A., Luxembourg, Luxembourg

[21] Appl. No.: 559,755

[22] Filed: Dec. 9, 1983

[51] Int. Cl.$^4$ .............................................. A61K 31/79
[52] U.S. Cl. ...................................... 424/80; 424/78; 514/223.2; 514/223.5; 514/629; 514/651; 514/653; 514/869
[58] Field of Search ................... 514/222, 869; 424/80

[56] References Cited

U.S. PATENT DOCUMENTS 3,476,858 11/1969 Nelson ................................. 514/222
3,781,430 12/1973 Cragoe ................................. 514/222

OTHER PUBLICATIONS

Diuretics Chemistry, Pharmacology, and Medicine, Edited by Edward J. Cragoe, Jr., John Wiley & Sons, 1983, pp. 76-97, 689, 690.
Handbook of Hypertension, vol. 1, Clinical Aspects of Essential Hypertension, edited by J. I. S. Robertson, Elsevier, 1983, pp. 404-409.

*Primary Examiner*—Paul R. Michl
*Attorney, Agent, or Firm*—Steinberg & Raskin

[57] ABSTRACT

Antihypertension action is achieved without diuresis by administration of a thiazide diuretic in an amount which while being sufficient to achieve antihypertension is insufficient to achieve diuresis. Such administration in a non-diuretic amount is effected in 4-8 consecutive hourly doses to achieve reduction of blood pressure without high urine output. The invention further relates to complexes of thiazides with mixed cation-anion exchange resins, to insoluble basic metal hydroxy thiazide salts, the salts of thiazide with calcium disodium edetate or disodium edetate, to molecular complexes of thiazides with long chain polymers such as hydroxy alkyl cellulose polymers, carboxy methyl cellulose and polyvinylpyrrolidone, to beta-adrenergic blocking amine-thiazide salts and to amiloride thiazide salts.

30 Claims, No Drawings

TREATMENT OF HYPERTENSION, COMPOUNDS AND COMPOSITIONS FOR ANTIHYPERTENSION AND DIURESIS

BACKGROUND OF THE INVENTION

More than twenty percent of the adult population present the symptoms and complaints of hypertension. In most cases of systemic hypertension, the pathogenesis of the disease is obscure and therapy is directed only toward the correction of the abnormal blood pressure.

Although such an empirical approach to the management of a serious disease state is far from ideal, it is clear that manometric success per se does favorably affect prognosis. It has been established that when the systolic and/or diastolic blood pressures are at the upper extreme of the presently accepted normal range, the risk of death of cardiovascular disease is greater for the patient and when the blood pressure rises above the normal range, the patient threat increases inordinately. Simply lowering the diastolic pressure to below 105 mm Hg. has been found to reduce the morbidity and mortality arising from a variety of cardiovascular complications.

Current therapy of hypertension is directed essentially toward the reduction of systemic blood pressure and because of such an omnibus approach no present single agent or treatment regimen has been found to be specific to either cure this disease or even to be consistently symptomatically effective in lowering blood pressure in the hypertensive patient.

Diuretic agents are among the most commonly used drugs in present day therapy to achieve a lowering of blood pressure and among the different diuretic agents used in the treatment of hypertension, the thiazide class of diuretic drugs is perhaps the most commonly administered diuretic substance. In its simplistic definition, diuretic substances are agents which increase the volume of urine output. However, by common usage the term diuresis has assumed two special connotations which comprise first, an increased urine volume output and secondly, a net loss of solute and water. While the renal physiology affecting these separate actions are independent of one another, there is an interaction between these effects which is reflected in the overall therapeutic response.

The thiazide diuretics are understood to act on the proximal kidney tubule to inhibit both water reabsorption together with sodium and chloride ions. The enhanced sodium ion load presented to the distal tubule segment also causes an increased loss of potassium ion and requires potassium supplementation, a major problem of diuretic therapy.

The composition of urine is the result of a complex series of secretory and reabsorptive functions performed by the renal tubule, the functional unit of the kidneys. Virtually all substances present in plasma are transported through the tubules wherein both excretory filtration as well as reabsorption occurs. The amount of a solute excreted into urine and the proportion reabsorbed in the tubule depend upon many diverse properties of the solute, as well as the integrity of kidney physiology.

In general, the rate of excretion of a solute through the kidneys will be proportional to its concentration in plasma. Substances that are in water-soluble polar form are excreted in urine, whereas compounds which are in a non-polar lipid-soluble form will be reabsorbed and recycled so that their therapeutic effect will persist as a function of the metabolic rate in the various systemic tissues. In the presence of high volume urine output, the blood levels of a drug are reduced, thereby lowering the pharmacologic intensity of the systemic effect.

At low urinary flow rates, a high tubular diffusion substance will be readily reabsorbed to retain or enhance its effect. Thus as urine flow increases under diuresis, back-diffusion becomes less significant and excretion is enhanced, to minimize and even negate important pharmacologic actions.

It has been recognized that the pH of urine dramatically influences the diffusion reabsorption rate for a particular compound. The extent to which a weak acid or weak base will be reabsorbed from renal tubular fluid will depend on its ionization constant, and the inherent lipid solubility of the molecular species. The lipid form of a compound is more readily reabsorbed and is less subject to excretion in urine.

As the pH of the urine decreases, a large fraction of a weak acid will be converted to the undissociated lipid form of the compound and conversely, as the pH rises, a larger fraction of a weak base will be present in the undissociated state. Thus weak acids are preferentially reabsorbed in the kidney at an acid pH value, but are excreted more readily as the urine pH becomes more alkaline, while bases are more readily excreted in an acid urine than when it is more alkaline.

These physiologic considerations of urinary excretion and reabsorption to maintain a constant plasma level become most significant for those compounds whose separate pharmacologic actions occur at particular threshold levels. High plasma threshold-level actions are obscured and even negated by a rapid depletion of the agent through increased urinary flow and solute loss. Increasingly large doses of a drug are then required to obtain the desired effect with the consequent occurrence of serious, noxious, unwanted side effects, in order to achieve the desired high threshold effect in the presence of diuresis.

Experimental studies have demonstrated that the bi-diretional transport of plasma solutes is also influenced by a selective competition at the appropriate tubular receptive site for either excretion or reabsorption and results in either an increased or decreased excretion of a plasma solute with a corresponding variation in the intensity of its pharmacologic response. The clinical finding that a thiazide diuretic drug may cause hyperuricemia, although it rarely exacerbates an acute attack of gout, suggests that this class of diuretic substances exerts a competitive biphasic action on uric acid secretion. Hyperuricemia induced in the course of high volume diuretic therapy is becoming more prevalent and is gaining increased concern.

In other recent studies, it was shown that the saluretic effect of hydrochlorothiazide is prevented by the prior administration of the compound, probenecid, but if the thiazide is given first, saluresis occurs even though the appearance of the thiazide in the urine is delayed by the later administration of probenecid. This effect demonstrates that the excretion of the thiazides occurs at a site other than that for saluresis and that the plasma concentration of the thiazide causing a systemic response, may be unrelated to the diuretic saluresis observed. While saluresis may be high, the systemic action of the thiazides may be low or even absent.

The transport of sodium ion is particularly important in the kidney management of hypertension. In the course of its normal activity the kidney regulates electrolyte balance primarily through the reabsorption of water and the sodium ion. The reabsorption of sodium salts is accomplished with the back diffusion of large amounts of water. The magnitude of such reabsorptive process is readily seen from the fact that approximately 180 liters of glomerural urinary filtrate is formed within a twenty-four hour period, but about 178–179 liters of which are reabsorbed, carrying with it nearly 1.2 kilograms of salt. This reabsorption of electrolytes and water is so carefully controlled that the osmolality, pH and electrolyte content of plasma and cellular fluids are constantly maintained within extremely narrow normal limits.

Reabsorption of sodium ions and corresponding amounts of water to render tubular fluid hypotonic is known to occur in the loop of Henle. Here, a process similar to that occurring in the proximal renal tubule takes place to provide a final adjustment of the electrolyte excretion in urine. Both sodium ion and water are reabsorbed but the reabsorption of electrolytes and water along the tubule is inversely related to the volume of urine excreted.

When large amounts of urine are excreted, as in the presence of potent diuretic substances, correspondingly increased amounts of sodium and other electrolytes are also excreted. It is important to recognize that thiazide diuretic agents have been shown to be without effect on the loop of Henle, and exert their saluretic effect through an action at another reabsorptive site as well as by high urine volume excretion.

There is a general agreement of the adverse relationship between sodium ion content in the blood and hypertension. This has given rise to the general therapeutic concept for a need to reduce plasma sodium ion levels. In fact, the antihypertensive action of the thiazide diuretics was originally thought to simulate the beneficial effects produced by low salt diets for the hypertensive patient through renal elimination of salt. However, long term balance studies have not supported the hypothesis that chronic sodium depletion adequately explains long term antihypertensive effects observed observed for this class of compounds. Newer experimental studies have indicated that thiazides may decrease the effects of catecholamines which would alter the electrolyte content of the vascular wall. However, an antihypertensive action occurring apart from the high volume diuresis has not been clinically demonstrated for diuretic agents and current therapy with diuretic drugs is based solely upon their respective diuretic potency and saluretic action.

In the course of development of a unified concept of the relationship between sodium ion reabsorption; acidification of urine and the role of carbonic hydrase inhibition in hydrogen ion and bicarbonate transport in the kidney the synthesis of potent chemical agents acting on the kidney, was accomplished. Chlorothiazide, the first thiazide compound synthesized, was shown to be a potent diuretic and saluretic agent. Following the clinical introduction of chlorothiazide, an expanded series of structurally related chemical compounds were synthesized, all having essentially the same pharmacology, but differing diuretic potencies.

Analogues to the earlier series of thiazide diuretic compounds, in which the heterocyclic ring was saturated (hydrothiazides) were subsequently prepared and shown to possess significantly greater diuretic potency. However, all thiazide compounds have common structural relationships and all are used on the basis of their common diuretic property. The structural similarities of the group of thiazide diuretic agents, together with their comparative properties are presented in Table I.

The natriuretic effect obtained with the separate thiazide derivatives is essentially similar for all thiazide compounds. Although the average daily diuretic does for the thiazide compounds ranges from 2000 mg. (2 grams) of chlorothiazide to about 2 mg. for cyclopenthiazide and cyclothiazide, there is little difference in either the magnitude of diuresis or saluresis obtained among the various compounds. The more potent agents have a relatively greater chloretic activity and may even cause a hypochloretic alkalosis in some patients. All thiazide compounds cause potassium loss which is directly related to the magnitude of sodium ion excreted rather than to the particular thiazide employed or its structure.

TABLE I

STRUCTURE, ACTIVITY, AVERAGE MINIMUM DIURETIC DOSE
OF THIAZIDE DIURETIC COMPOUNDS
Prototype Structures

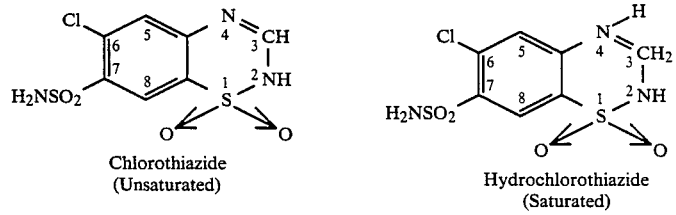

Chlorothiazide
(Unsaturated)

Hydrochlorothiazide
(Saturated)

| Thiazide Group of Compounds | Substituents in Position* | | | | Carbonic** Anhydrase Inhibition | Approx.*** Natriuretic Activity | Daily Diuretic Dose (mg) |
| --- | --- | --- | --- | --- | --- | --- | --- |
| | 2 | 3- | 5- | 6- | | | |
| Chlorothiazide | H | H | H | Cl | 7.6 | 1 | 2000 |
| Flumethiazide | H | H | H | $CF_3$ | 0.3 | 1 | 200 |
| Benzthiazide | H | $CH_2SCH_2C_6H_5$ | H | Cl | 36.0 | 10 | 200 |
| Hydrochlorothiazide | H | H | H | Cl | 0.6 | 10 | 200 |
| Hydroflumethiazide | H | H | H | $CF_3$ | 0.08 | 10 | 200 |
| Bendroflumethiazide | H | $CH_2C_6H_5$ | H | $CF_3$ | 0.04 | 100 | 20 |
| Polythiazide | $CH_3$ | $CH_2SCH_2CF_3$ | H | Cl | 2.0 | 200 | 8 |
| Methyclothiazide | $CH_3$ | $CH_2Cl$ | H | Cl | 2.5 | 100 | 10 |
| Trichlormethiazide | H | $CHCl_2$ | H | Cl | 0.25 | 200 | 8 |

TABLE I-continued
STRUCTURE, ACTIVITY, AVERAGE MINIMUM DIURETIC DOSE
OF THIAZIDE DIURETIC COMPOUNDS
Prototype Structures

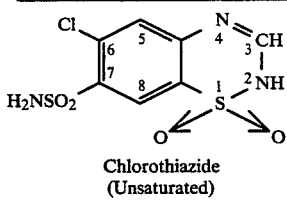

Chlorothiazide
(Unsaturated)

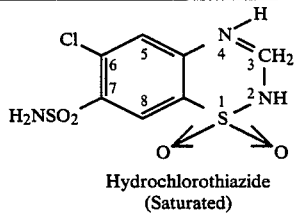

Hydrochlorothiazide
(Saturated)

| Thiazide Group of Compounds | Substituents in Position* | | | | Carbonic** Anhydrase Inhibition | Approx.*** Natriuretic Activity | Daily Diuretic Dose (mg) |
|---|---|---|---|---|---|---|---|
| | 2 | 3- | 5- | 6- | | | |
| Cyclothiazide | H | (5-norbornen-2-yl) | H | Cl | 0.5 | 500 | 2 |
| Cyclopenthiazide | H | cyclopentylmethyl | H | Cl | 1.0 | 1000 | 2 |

*The 7-position is always substituted with a sulfonamide group in all thiazide compounds.
**Carbonic Anhydrase Inhibition values are stated as a ratio of sulfonilamide having a value of 1.
***The natriuretic activity reported is based upon a comparison with chlorothiazide having a value of 1.

All of the thiazide derivatives inhibit carbonic anhydrase to some extent, but this inhibitory activity does not correlate with the compound's activity as a diuretic agent. Cyclopenthiazide is only 1/10th as active as chlorothiazide as a carbonic anhydrase inhibitor but is a thousand times more potent as a diuretic and natriuretic agent. On the other hand, the carbonic anhydrase inhibition observed for the different thiazide compounds does not correlate with their ability to block bicarbonate reabsorption. Benzthiazide is a relatively potent carbonic anhydrase inhibitor, but it does not cause an appreciable clinical alkalinization of urine but rather produces the excretion of nearly equivalent amounts of sodium ion and chloride ion.

In clinical use all thiazide diuretic agents are considered to be of equal effectiveness, both as diuretics and as antihypertensive agents. Although the specific daily dosage will vary for different thiazide compounds and some have a longer half-life than others, and some may cause different levels of chloride ion loss, there is no evidence that these agents differ either in their safety or in their basic mode of action from the prototype compound, chlorothiazide. The adverse effects, especially those involving potassium depletion and patient morbitidy are observed with all of the members of this class.

It has been proposed that the diuretic potency of the thiazide group, which ranges in activity from chlorothiazide being one and cyclopenthiazide as a thousand, is correlated with lipid-solubility of the respective compound and is inversely related to renal clearance of the agent. The observation that a thiazide acts on different receptor sites of the kidney to cause specific actions and pharmacologic responses raises the question that these compounds may also act on systemic receptor sites to cause other systemic actions which as yet remain unknown. The current clinical use of these diuretic compounds in the management of hypertension is solely directed toward achieving high urinary output.

SUMMARY OF THE INVENTION

It is an object of the present invention to provide anti-hypertension action without diuresis by proper dosage and administration of thiazide diuretic compounds.

It is another object of the present invention to provide for the protection of thiazide compounds against the polarizing influence of gastric acidity by the formation of mixed cationic-anionic resin-thiazide adsorbate complexes, and to provide for the use of such complexes to effect diuretic action with antihypertensive action or to effect antihypertensive action alone without diuresis.

It is a further object of the present invention to provide for the protection of thiazide compounds from the ionizing effect of strong acids by the provision of insoluble basic hydroxy metal thiazide salts, and to provide for effecting diuresis therewith, antihypertensive action or antihypertensive action without diuresis.

It is another object of the present invention to provide protection of thiazide compounds from polar excitation due to mineral and other substances by the provision of salts of thiazides with calcium disodium edetate or sodium edetate and also to provide mixtures of thiazides with calcium disodium edetate or disodium edetate for this purpose. The invention still further provides for the use of such salts and mixtures to achieve diuretic action with antihypertension or to achieve antihypertension without diuretic action.

In accordance with a further object of the present invention the ionizing effects of gastric acidity on thiazide compounds is protected by the formation of molecular complexes between thiazides and long chain polymers such as hydroxy alkyl cellulose polymers, carboxy methyl cellulose and polyvinylpyrrolidone. The invention further comprises the use of such complexes to effect diuretic action with antihypertension and to effect antihypertension without diuretic action.

It is still a further object of the present invention to provide augmented antihypertensive action by the administration with a thiazide salt of a beta-adrenergic blocking agent.

It is yet another object of the present invention to provide compounds of thiazides and beta-adrenergic blocking agents and to effect antihypertensive action without diuresis by the administration thereof.

It is still a further object of the present invention to provide salts of thiazides with amiloride which have improved antihypertensive action.

Other objects and advantages of the present invention will be apparent from a further reading of the specification and of the appended claims.

It was unexpectedly found that a systemic antihypertensive action, which is dissociated from the diuretic action on the kidney, will be obtained after the administration of an amount of a thiazide agent which is substantially below the effective diuretic dose but which can nevertheless effect antihypertensive action and thus to achieve antihypertension without diuresis. This new approach to treating hypertension results in a more effective and advantageous method since the well-known noxious effects of high potency diuresis are avoided. It was found that when from 7% to 25% of the diuretic dose of a thiazide compound is administered, preferably in from 4 to 8 consecutive hourly doses, once or twice daily, that a clinical lowering of blood pressure results without the detriment of an increased urine volume output.

In this manner, potassium loss is avoided; patient disability and sleep interruption, because of frequent micturition is not encountered, and vitamin and mineral washout avoided. Patient compliance is high and the salutory effects of lowered blood pressure are readily observed. Such antihypertensive action dissociated from the diuretic action for the thiazide compounds represents a hitherto unknown pharmacologic effect and constitutes an important therapeutic advance since it enables a positive approach to achieve a lowering of blood pressure, without patient detriment.

Thus, it has been found that the administration of an appropriate amount of a thiazide diuretic compound which is significantly less than the diuretic dose required to produce elevated urinary output, resulted in a lowering of blood pressure. Such dosage was preferably administered at hourly intervals over a period of from 4 to 8 hours to hypertensive patients. In this manner, a favorable clinical manometric response was observed without the occurrence of diuresis and its consequent noxious effects. Long term clinical usage of these compounds is facilitated since potassium loss may be generally avoided and the occurrence of alkalosis virtually never encountered. Since the absence of diuresis permits uninterrupted sleep and otherwise alleviates morbidity of the patient arising from frequent micturition, better patient compliance with therapy results.

While the exact mechanism of the clinically advantageous dissociated antihypertensive effect observed in the absence of a diuretic action when the low dose thiazide compositions are administered has not been fully defined, it may be postulated that the observed lowering of blood pressure reflects a hitherto unknown systemic vascular response of the thiazide, apart from the kidney, and involves a modification of systemic vasomotor tone. This is consistent with the evolving knowledge of the pharmacologic activity of the thiazide compounds to indicate that these agents act upon systemic receptor sites to result in specific actions and that these may be obscured by high diuretic potency. Thus, for example, it has been shown that the administration of a thiazide compound will depress sexual function, an action apart from the kidney.

The antihypertensive action that we have found to be dissociated from the diuretic activity of the thiazides, has not been earlier observed because the potent diuresis causes a washout of the drug thereby depleting the plasma blood level to interrupt or prevent its action at the systemic receptor site affecting vasomotor tone. In the absence of the diuretic effect, this novel pharmacologic response becomes dominant. However, because of the normal excretion of the thiazides, together with metabolic inactivation and the short half-life of the thiazide compounds, thiazide supplementation is required to maintain steady-state saturation levels. Frequent administration of the sub-diuretic dose of the thiazide compound is necessary to enable tissue receptor site saturation to achieve the desired modification of vasomotor tone with its consequent lowering of blood pressure.

It is known that the half-life duration of activity for the separate thiazide compounds ranges from 3 hours to 6 hours after administration of a single dose, with the half-life peak effect occurring within 1.5 to 2.0 hours after administration of the dose. This half-life period is dependent upon the metabolic inactivation of the particular thiazide compound together with its rate of excretion through the kidney and other routes. The metabolic inactivation and excretory loss of the compound depletes the plasma blood level of the active ingredient thereby effecting the steady state concentration of active substance at the vasomotor receptor site.

Ordinarily such plasma drug loss is compensated for by the administration of dose overage. However, since a critical fractional low dosage range is required to achieve the antihypertensive effect dissociated from diuresis, then compensation for the metabolic inactivation and systemic excretion of the compound cannot be corrected by dose elevation. It was found that the metabolic inactivation and systemic excretion may be satisfactorily overcome by administering repeat doses at hourly intervals for a period of from 4 to 8 hours until receptor site saturation occurs. This hourly dose supplementation assures the maintenance of a steady state plasma level without exceeding the critical diuretic threshold to achieve the desired antihypertensive effect.

It was found that the unit dose of the selected thiazide compound necessary to achieve a lowering of the blood pressure dissociated from diuresis, will be from about 7% to 25% by weight, of the diuretic dose for the respective thiazide compound when such dosage is administered at hourly intervals for at least 4 doses and not exceeding 8 consecutive dises, once or twice daily. The particular amount of the respective thiazide compound used to manufacture the unit dose is further influenced by certain chemical and physiologic forces which modify its absorption pattern as well as the individual patient's level of sensitivity of the systemic receptor site to a particular thiazide compound.

Further improvement in the use of thiazide compounds by the protection thereof from the actions of substances in the gastrointestinal tract are desirable.

The thiazide compounds behave as non-ionized acids and are preferentially absorbed in their free, lipid-soluble, non-ionized acid form. Thus, salt-forming and polar ionizing moieties encountered in the gastrointestinal tract will increase the polarity of a thiazide compound to change its ionizing characteristics to modify its absorption pattern.

Another force impeding the absorption of the thiazide compounds is the shift in the dynamic equilibrium resulting from proton interchange with the protein amino groups and/or hydroxyl groups of carbohydrate substances. The dynamic equilibrium formed under the changing conditions encountered physiologically causes a proton-electron transfer between the non-ionic lipid-soluble free form and the weakly charged acid ionized form of the thiazide compound.

The proportion of the ionized thiazide form that is present will impact on the absorption potential of the thiazide molecule across the gastrointestinal tract with the lipid-soluble nonionized form being preferentially absorbed. The amount absorbed and its steady-state blood level will be reflected in the response at the systemic vasomotor receptor site. It was found that certain measures could be taken to preferentially shift the equilibrium in the direction to preserve the non-polarized, free-acid, lipid soluble form of the thiazide against polarizing forces.

Protection of the thiazide compound may be obtained by forming an adsorbate compound, comprising a high capacity, mixed cation-anion exchange resin, as for example, the Amberlite ion exchange resins available as an article of commerce from the Rohm and Haas Company, Philadelphia, Pa., and the selected thiazide. Such compounds are obtained by precipitating the free acid form of the thiazide, e.g. by reacting a water-soluble metallic salt of the selected thiazide compound, as for example the sodium salt, in aqueous solution with an acid such as hydrochloric acid and reacting one part of the free acid form of the thiazide with two parts by weight of the anionic Amberlite resin, stirring for about 15 minutes, filtering and drying the infiltrate solid to recover the formed thiazide resin adsorbate compound. This adsorbate may be used directly or preferably mixed with one part by weight of a high capacity cationic Amberlite resin, to reinforce the protective action against ionization arising from salts in the gastrointestinal tract. Under certain conditions, the mixed high potency cationic-anionic Amberlite resin may be used directly to form the adsorbate thiazide compound. The mixture is then treated as a single absorption resin when used to prepare the resin thiazide adsorbate salt and the same proportions are used.

The mixed cationic-anionic resin-thiazide adsorbate salt provides protection against the polarizing influence of the gastric acidity. Since hydrochloride acid is a stronger acid than the thiazide compound, it is capable of displacing the absorbed weaker thiazide acid form from the resin. The displaced thiazide would then have an increased polarity to modify the absorption pattern of the thiazide released from the unit dose.

An alternate means to protect the lipid-soluble acid thiazide compound from the ionizing effect of stronger acids and salt forming moieties in the gastric pouch is to administer the respective thiazide compound in the for of the insoluble basic hydroxy metallic salt. Such a compound preferentially buffers the immediate acid environment surrounding the thiazide salt by maintaining a protective pH mantle at a level wherein the polar stimulation of the thiazide is suppressed.

Insoluble basic hydroxy metal thiazide salts may be formed through the reaction of the selected thiazide compound with a suitable metallic oxide, hydroxide, or carbonate and bicarbonate salt selected from the group of metals consisting of aluminum, calcium and magnesium in suitable molar proportions. The formed compound is recovered, dried and used to prepare the unit dosage form, in a sufficient amount based upon the respective thiazide content.

Ethylene diaminetetraacetic acid or edetic acid, calcium disodium edetate, and disodium edetate have the ability to form water soluble complexes with alkaline earth ions and basic substances which involve a coordinate linkage between metal ions, carboxyl groups and nitrogen. This complexing action of the salts of edetic acid prevent precipitation and activation by basic ions of the free acid thiazide, thereby preserving its non-polar lipid soluble form. While the formation of the calcium disodium edetate salt of the appropriate thiazide compound is a preferred means to protect the compound from polar excitation by diverse mineral and other substances in physiologic fluids, a similar effect was found when the disodium thiazide edetate salt is used. A satisfactory protective effect was also observed when these agents are used in admixture with the appropriate thiazide compound, although the formed complex salt remains a preferred protective compound.

Still another method to avoid the ionizing effects of gastric acidity on the selected thiazide compound so that it retains its lipid-soluble, non-polar characteristics is to form a molecular complex between a long chain polymer as for example, a hydroxyalkylcellulose polymer, a carboxymethylcellulose or polyvinylpyrrolidone. These polymeric substances are capable of forming protective molecular complexes with the respective thiazide compound, which complexes resist acid polarizing activity. The formed complexes are reversed in the lower intestinal tract where the more alkaline pH favors the absorption of the lipid-soluble, non-polar thiazide form.

The internal colloidal cellulose-thiazide molecular complex is formed by dispersing one part by weight of an appropriate colloidal cellulose polymer, such as hydroxymethylcellulose, carboxymethylcellulose or sodium carboxymethylcellulose, in a sufficient quantity of water to form a colloidal solution and while warming to about 50° C., adding a methanol solution of one-half part by weight of the selected thiazide compound based on the weight of cellulose polymer used. The mixture is stirred and the solvent evaporated. The residue is dried and comprises the molecular complex formed between the respective cellulose polymer used and the selected thiazide compound.

Another type of protected polymer complex is obtained by reacting the thiazide with polyvinylpyrrolidone. Polyvinylpyrrolidone is a synthetic polymer, consisting essentially of linear 1-vinyl-2-pyrrolidone groups, having an average molecular weight of from about 10,000 to 700,000 and is capable of forming a molecular complex with a thiazide diuretic compound to provide a protective colloid action for the thiazide compound, preserving the non-polar lipid soluble acid form in the gastrointestinal tract.

The molecular complex of the appropriate thiazide compound with the polyvinylpyrrolidone polymer is formed by reacting one part by weight of the selected thiazide compound with five parts by weight of the polyvinylpyrrolidone. The reactants are dispersed separately in the selected solvent as for example, water, an alcohol of the formula ROH, wherein R is an alkyl group of from 1 to 5 carbons in chain length or mixtures of these, and mixed while stirring. The mixture is warmed to about 50° C. until a clear colloid gel solution results. After cooling to room temperature, and the solvent removed in vacuo, the formed molecular complex, polyvinyl-pyrrolidone-thiazide is isolated as a glassy plate, which is then ground to a No. 60, or finer, standard mesh screen size powder for formulating into unit dosage form or may be used directly.

The formed polyvinylpyrrolidone-thiazide molecular complex is essentially chemically inert and dispersible in water. The polyvinylpyrrolidone-thiazide molecular complex is virtually unchanged by dilute acids, but mild alkaline conditions will reverse the molecular complex to liberate the thiazide moiety in its lipidsoluble form.

It was further found that the concurrent administration of certain beta-adrenergic receptor blocking amines and a thiazide compound will sensitize the vascular system receptor site to the antihypertensive action of the thiazide compounds which is reflected in vasomotor tome, to result in a synergism. The synergized augmentation of the non-diuretic, antihypertensive effect is evident in the reduced quantity of thiazide compound administered to achieve the antihypertensive effect; the intensity of the basomotor action; the fewer number of consecutive doses required to achieve the desired effect; the persistance of the response and the extension of the half-life of the thiazide compound.

Preferably this synergism is achieved by administering the compound formed between the selected beta-adrenergic blocking agent and the appropriate thiazide compound, but the simultaneous administration of the mixture of these components will also result in the desired synergised effect. The suitable beta-adrenergic blocking amine compounds used to prepare the corresponding thiazide salt are set forth in Table II.

TABLE II
CHEMICAL STRUCTURE OF THE BETA ADRENERGIC BLOCKING AMINES

| B-BLOCKING AGENT | CHEMICAL NAME |
| --- | --- |
| Alprenolol | 1-[(1-Methylethyl)amino]-3-[2-(2-propenyl) phenoxy]-2-propanol. |
| Butidrine | 5,6,7,8-Tetrahydro-a[[(1-methylpropyl)amino]-methyl]-2-naphthalenemethanol hydrochloride. |
| Butoxamine | a-[1-[1-(1-Dimethylethyl)amino]ethyl]-2-5-dimethoxybenzenemathanol. |
| Dichloroisoproterenol | 3,4-Dichloro-a-[[(-methylethyl)amino]methyl] benzemethanol. |
| Nifenalol | (+)-a-[[(Methylethyl)amino]methyl]-4-nitrobenzenemethanol. |
| Oxyprenolol | 1-[(Methylethyl)amino]-3-[2-(2-propenyloxy) phenoxy]-2-propanol. |
| Practolol | N—[4-[2-Hydroxy-3-[(1-methylethyl)amino] propoxylphenyl]acetamide. |
| Pronethalol | a-[(Isopropylamino)methyl]-2-naphthalene-methanol. |
| Propanolol | 1-(Isopropylamino)-3-(1-naphthyloxy)-2-propanol; propanolol. |
| Sotalol | N—[4-[1-Hydroxy-2-[(1-methylethyl)amino] ethyl]phenyl]methanesulfonamide. |
| Toliprolol | 1-(Isopropylamino)-3-(m-tolyoxy)-2-propanolol. |

The compound formed between the beta-adrenergic receptor blocking agent and the appropriate thiazide compound is obtained by reacting the appropriate beta-adrenergic receptor blocking amine hydrochloride with the sodium or metallic salt of the selected thiazide compound in the proportion of from 1 to 1.5 parts by weight of beta-adrenergic receptor blocking amine hydrochloride for each part by weight of the selected sodium or metallic thiazide salt. The reaction may be conducted in any suitable inert solvent. The dissolved reactants are mixed and after warming to about 50° C. for about ½ hour, the formed salt isolated. While the hydrochloric acid salt of the beta-adrenergic blocking amine is a preferred reactant for this reaction, any other acid salt of the selected amine compound may be used in its place in the same molar proportions.

The beta-adrenergic-blocking amine exists in the form of both the d-and l-isomers. Although the l-isomer is considerably more potent than the d-isomer as to its beta-adrenergic blocking activity, both isomers are approximately equal in their properties enhancing the antihypertensive action of the sub-diuretic dose of the thiazide compound. Accordingly, either the dl form or the separate d- and l-isomers of the appropriate beta-adrenergic blocking amine may be used to form the appropriate thiazide in order to achieve the desired synergism.

Although the reaction between sodium salt of the selected thiazide compound with an acid salt of the selected beta-adrenergic blocking amine compound is a preferred means to obtain the desired beta-adrenergic blocking amine-thiazide salt, an alternate means to obtain this salt is by the direct reaction of the acid thiazide compound with the amine. While this reaction requires a longer processing time, it nevertheless results in the same compound.

When used in therapy, the formed beta-blocking aminethiazide salt is administered on the basis of thiazide content in an amount of from 7% to 25% of the average diuretic dose of the respective thiazide moiety in from 4 to 8 consecutive hourly doses, once or twice daily.

Amiloride or 3,5-diamino-N-aminoiminomethyl-6-chloropyrazenecarboxamide, is a potassium sparing diuretic agent which has been administered together with the sodium salt of the hydrochlorothiazide to minimize potassium loss. Amiloride, when used with sodium hydrochlorothiazide is always administered as a mixture of two separate diuretic agents, each exerting an independent and separate action on the kidney.

It was found that the compound formed between amiloride and the appropriate thiazide compound possesses new chemical and physiologic properties to provide a more intense antihypertensive action. The formed amiloride-thiazide salt is obtained by dissolving one part by weight of the selected thiazide sodium salt in methanol, which is reacted with a methanol solution of 1.5 parts by weight of amiloride hydrochloride. The mixture is warmed to 50° C. with stirring and filtered. The solvent is concentrated to one-third its volume and set aside to crystallize in the ice chest. The formed crystals are isolated and comprise the formed amiloride-thiazide salt. A clinically preferred dosage range in unit dose form to achieve the desired antihypertensive action with the newly formed amiloride-thiazide salts is from 0.1 to 10 mgm of the formed compound when administered from 4 to 8 consecutive doses, once or twice daily.

The advantage of the formed amiloride-thiazide salt to achieve the desired antihypertensive effect is readily seen when the daily dose of the formed salt amiloride-hydrochlorothiazide is compared with the daily dose required for the mixture of amiloride and hydrochlorothiazide to achieve an antihypertensive effect. When amiloride is administered concurrently with hydrochlorothiazide as a mixture of separate components, the dose of active ingredients is about 210 mg. per day and causes a strong diuretic response with all of the limitations associated with diuresis. In contrast to this, the formed amiloride-hydrochlorothiazide salt is administered in a daily dose of about 50 mg., depending upon the patient's need, to achieve the desired antihypertensive action but without diuresis and its untoward side effects.

It will be found that in practice, the dissociation of diuresis and its noxious untoward effects, from the desired systemic antihypertensive vasomotor action of a thiazide compound will result after the administration of from 4 to 8 consecutive hourly doses, once or twice daily, of a sufficient quantity of a selected thiazide compound in unit dosage form.

The desired effects of the present invention can be achieved by the administration of:

(a) from 7% to 25% of the effective diuretic dose of the selected thiazide compound, or (b) a mixed cation-anion-resin-thiazide adsorbate salt, or, (c) a hydroxymetal thiazide salt, or, (d) a calcium disodium thiazide edetate salt or disodium thiazide edetate salt, or (e) a hydroxyalkylcellulose thiazide complex or carboxymethylcellulose thiazide complex, or (f) the povidone thiazide molecular complex, or, (g) a beta-adrenergic receptor blocking amine-thiazide salt, or.

(h) an amiloride-thiazide salt.

The pharmaceutically acceptable unit dose compositions are prepared to contain a sufficient quantity of the selected thiazide active ingredient to provide not less than 7% by weight and not more than 25% by weight of the diuretic dose of the selected thiazide compound. It will be observed that when the thiazide content of the unit dose falls below 7% of the diuretic dose for the particular thiazide compound selected, then the desired dissociated antihypertensive action will not be realized. When the unit dose of the thiazide compound is greater than 25% of the diuretic dose for the thiazide compound selected, then diuresis and certain of the adverse properties associated with diuresis will occur to detract from the overall advantages of the present invention.

The amount of a particular active ingredient contained in unit does form to achieve the dissociated diuretic effect is unrelated to the specific diuretic potency of the compound, but is influenced by its absorption in its lipid soluble free acid form; the sensitivity of the systemic vasomotor receptor sites and the relative antihypertesnive response of the patient to the particular thiazide compound selected as well as the relative intensity of the hypertensive status of the patient. The mild-to-moderate hypertensive patient will require a lesser amount of the active ingredient, while the patient with severe hypertension will require a higher dose within the range described to achieve the favorable blood pressure lowering effect.

The desired thiazide unit dose is administered in from 4 to 8 consecutive hourly doses, once or twice daily. When less than 4 hourly doses are administered, the most favorable manometric changes are not always observed and when more than 8 consecutive hourly doses are administered, diuresis with its consequent limitations can begin.

All of the pharmaceutically acceptable thiazides are relatively rapidly absorbed through the gastrointestinal tract and a demonstrable effect is observed within the first hour after oral administration. While the unsaturated thiazides are rapidly excreted within 3 to 6 hours, certain saturated thiazides, as for example, bendroflumethiazide, polythiazide, methylclothiazide, trichlormethiazide, cyclothiazide and cyclopenthiazide, show proportionately high binding to plasma proteins and therefore may show relatively longer durations of action.

All of the pharmaceutically acceptable thiazides are excreted in the proximate tubule, and renal clearances of these drugs are high so that an individual thiazide compound clearance may be either above or below the plasma filtration rate. In view of the critical low dose-range of the active ingredient required to achieve the dissociated-diuretic antihypertensive effect, the individual variations in the clearance rate for the different thiazide compounds which affect the steady-state, plasma levels are compensated for by the repeated hourly unit dose administration of between 4 to 8 doses.

It will be readily seen that some patients may experience inconvenience with a regimen requiring a number of consecutive hourly doses over a maximum period of eight hours and may omit a dose in the regimen, or may require treatment at night and be awakened from sleep. Such inconvenience may be readily avoided through the use of the conventional timed-released dosage forms as the unit dose carrier for the active ingredient. The desired amount of the active ingredient is formulated into the timed release dosage form so that the active ingredient is released in predetermined amounts at hourly intervals after ingestion. Such timed-release dosage forms are well known in the art and may be readily formulated to contain an appropriate amount of the selected active thiazide compound in a single tablet or capsule unit dose so that the desired amount of active ingredient will be released at hourly intervals for the indicated number of hours.

The use of such timed-release vehicles to administer the selected unit dose of the particular thiazide agent at hourly intervals results in an identical manometric lowering of blood pressure as is obtained when the immediate release unit dosage forms are administered for the same time frame. However, the timed-release dosage forms have an added advantage over the immediate release dosage form in obtaining patient compliance with a difficult regimen, reducing the nursing time necessary to administer the medication to the infirm and elderly patient, and together with the assurance that the patient will not omit a dose in the prescribed sequence.

While solid dosage forms such as tablets or capsules will be preferred, liquid preparations may be used in accord with the patient's need. Tablets or capsules may be prepared to contain the appropriate amount of the selected thiazide active ingredient, mixed with pharmaceutically acceptable diluents and either compressed into tablets of appropriate size and shape or filled into capsules. Liquid preparations may be prepared in the form of a syrup, hydroalcoholic tincture or as an aqueous solution utilizing conventional liquid vehicles and preparative procedures as are well known in the art.

When preparing the particular unit dosage form, it is necessary that the pharmacologically sufficient quantity of the selected active ingredient be present in the lipid soluble free acid form and that it be protected against polarizing activity by the gastrointestinal contents, to enable more complete and uniform absorption of the selected active compound.

Tablet and capsule unit dosage forms are prepared by mixing the appropriate weight of the selected active ingredient with a pharmaceutically suitable diluent such as starch or sugar. The mixture is then granulated with a binding agent, such as a higher alkyl alcohol having the formula ROH wherein R is from 10 to 18 carbon atoms in chain length. The amount of such alkyl alcohol binding agent used is at least one percent by weight of the finished tablet weight.

Ethylenediaminetetra-acetic acid (EDTA) or its disodium salt (disodium edetate) in an amount of from 0.1% to 0.3% by weight of the finished tablet weight, is intimately mixed with the granulate and the mass tableted. When disodium edetate is used, this is rapidly converted to EDTA in the stomach, and preferentially combines with the alkali metal salts present in the gastic contents to minimize their polarizing activity, thereby preserving the lipid soluble form of the active ingredient.

Tablets of suitable size and shape are compressed, each containing the desired amount of selected active ingredient. When capsules are preferred, then the composition obtained just prior to compression into tablets is filled into an appropriate sized gelatin capsule to provide the unit dose capsule for use in therapy.

Sustained release preparations or timed-release dosage forms are prepared so that the amount of selected active ingredient is released in each hour as would be present in the immediaterelease unit dosage form, and to be repeated at hourly intervals for the appropriate number of doses.

DESCRIPTION OF PREFERRED EMBODIMENTS

The following examples are given to further illustrate the present invention. The scope of the invention is not, however, meant to be limited to the specific details of the examples.

EXAMPLE 1

To dissociate the antihypertensive vasomotor activity of a thiazide compound from its diuretic action in humans and animals, a pharmaceutical unit dose composition comprising the lipid soluble, free acid form of the selected thiazide compound is prepared to contain an amount of the selected thiazide agent of from 7% to 25% by weight of the diuretic dose, with the preferred amount being:

| COMPOUND | RANGE UNIT DOSE AMOUNT (mg) | | | RANGE DIURETIC DOSE (mg) |
|---|---|---|---|---|
| | PREFERRED | LOW | HIGH | |
| Chlorothiazide | 85.0 | 35.0 | 500.0 | 500-2000 |
| Flumethiazide | 80.0 | 35.0 | 250.0 | 50-1000 |
| Benzthiazide | 5.0 | 1.75 | 12.50 | 25-50 |
| Hydrochlorothiazide | 5 | 1.75 | 25.0 | 25-100 |
| Hydroflumethiazide | 5 | 2.0 | 12.5 | 25-50 |
| Bendroflumethiazide | 0.5 | 0.15 | 1.25 | 2-5 |
| Polythiazide | 1.0 | 0.30 | 2.0 | 4-8 |
| Methylclothiazide | 1.0 | 0.35 | 2.5 | 5-10 |
| Trichlormethiazide | 1.0 | 0.35 | 2.0 | 4-8 |
| Cyclothiazide | 0.75 | 0.07 | 1.5 | 1-6 |
| Cyclopenthiazide | 0.75 | 0.07 | 1.5 | 1-6 |

The unit dose is administered in from 4 to 8 consecutive hourly doses, once or twice daily.

If a sustained or timed release unit dose form is desired, then it is prepared so that the indicated unit dose quantity of the selected thiazide agent is released each hour in the amount set forth above for the appropriate number of hourly doses.

Chlorothiazide tablets are prepared by mixing 170 gm. of chlorothiazide with 350 gm. of lactose and 10 gm. of stearyl alcohol. The mixture is granulated with ethanol and screened through a No. 60 standard mesh sieve and 1.0 gm. of disodium edetate is added. The granules are compressed into tablets of suitable size and shape to provide 170 mg. of chlorothiazide in each tablet.

In a similar manner, tablets of the other thiazide compounds may be prepared using the amount of active ingredient set forth above for the appropriate compound, together with the same proportions of diluent, binding agent and disodium edetate.

When capsules are preferred then the mass obtained just prior to the compression step is filled into suitable gelatin capsules so that the unit dose capsules contain an amount of the appropriate thiazide compound as described above.

A unit dose tablet or capsule is preferably administered for 6 consecutive hourly doses although some patients may require 4 consecutive hourly doses and other, 8 hourly consecutive doses, once or twice daily.

EXAMPLE 2

The Preparation Of The Mixed Cation-Anion Resin Thiazide Complex

An aqueous solution prepared by dissolving 3.4 gms. of sodium chlorothiazide, 6-chloro-7-sulfamoyl-2H-1,2,4-benzothiadiazin2-yl-sodium, 1,1-dioxide, in 30 ml. of distilled water, is carefully titrated with 0.01N hydrochloric acid until the pH of the solution is between pH 3 and pH 4. The solution turns cloudy because of the colloidal precipitation of the insoluble free acid form of chlorothiazide.

Under vigorous stirring, 6.8 gms. of a high capacity anion-exchange-resin of the type known as "Amberlite" ion exchange resins, which are available as articles of commerce from the Rohm & Haas Company, Philadelphia, Pa., are added, and the mixture allowed to stand at room temperature for about fifteen minutes while stirring. The insoluble solid is filtered to recover the formed anion-resin chlorothiazide adsorbate compound, which is air-dried.

While the Amberlite ion exchange resins, as described above are preferred, there may be substituted in equal amount by weight, any of the other commercially-available high capacity ion exchange resins of the anionic-cationic types, care being taken that these resins are of high absorption capacity and being suitable for pharmaceutical use, for administration to humans and animals.

To the recovered, dried chlorothiazide-anion-resin adsorbate compound is added 3.4 gms. of a high capacity cation-exchangeresin and the mixture tumbled until a uniform distribution results. The formed mixed cation-anion-resin-chlorothiazide adsorbate is ground to a No. 60 standard mesh size or finer, powder, and may be used to prepare the desired unit dosage form. Each tablet, capsule or liquid unit dosage form is prepared to contain a sufficient quantity of the mixed cation-anion chlorothiazide resin complex to provide 170 mg. of chlorothiazide content per unit dose, which is administered in from 4 to 8 consecutive hourly doses, once or twice daily.

In place of the sodium chlorothiazide described above, any water-soluble metal salt of chlorothiazide may be substituted in molar equivalent amount and the acid titration is conducted as set forth above. The remainder of the steps are the same.

The lipid soluble free acid form of chlorothiazide may be used directly to form the appropriate resin-chlorothiazide compound complex. A colloidal dispersion of chlorothiazide, is obtained by dissolving 3.0 gms. of chlorothiazide in a sufficient quantity of methanol. The methanol solution of chlorothiazide is slowly added to 20 volumes of distilled water, with vigorous stirring, to form the colloidal dispersion. To this dispersion is added 6.0 gms. of the Amberlite anion-exchange resin while stirring. The formed chlorothiazide anion exchange resin adsorbate complex is recovered and dried.

To the recovered, dry anion-resin chlorothiazide complex is added 3.0 gm. of a cation exchange resin and the mixture tumbled until a uniform distribution results, which is then ground to a No. 60 standard mesh size or finer, powder and used to prepare the desired unit dosage form, containing a sufficient quantity of the mixed cation-anion chlorothiazide complex to provide 170 mg. of chlorothiazide complex to provide 170 mg. of chlorothiazide content per unit dose, administered in from 4 to 8 consecutive hourly doses, once or twice daily.

The mixed cation-anion resin chlorothiazide compound complex may be prepared directly from either the commercially-available mixed cation-anion exchange resin or with an extemporaneously prepared mixture of the appropriate resins. The preferred proportion of anion exchange resin to cation exchange resin used to prepare the mixed ion exchange resins is 2:1. The mixed cation-anion exchange resin is packed into a glass column and the colloidal dispersion of chlorothiazide, prepared as described above, is passed through the column. The effluent fluid is recycled until it is free of chlorothiazide content. The contents of the resin column are recovered, dried and comprise the formed mixed cation-anion exchange resin chlorothiazide adsorbate complex which is ground to a suitable powder size for use in preparing the unit dosage form as described above.

In a similar manner, the mixed cation-anion exchange resin adsorbate complex may be formed with the other thiazide compounds, utilizing the same procedures as described above, but substituting for the chlorothiazide a sufficient quantity of another thiazide compound as set forth in Example 1 together with the proper amount of the appropriate resin described below. The preferred weights of reactants required to form the appropriate thiazide cation-anion resin absorption complex are as follows:

| Thiazide Compound | Weight of Thiazide Compound | Weight of Anion Exchange Resin | Weight of Cation Exchange Resin | Weight of Mixed Cation-Anion Exchange Resins |
|---|---|---|---|---|
| Flumethiazide | 33 gms. | 66 gms. | 33 gms. | 99 gms. |
| Benzthiazide | 43 gms. | 86 gms. | 43 gms. | 129 gms. |
| Hydrochlorothiazide | 30 gms. | 60 gms. | 30 gms. | 90 gms. |
| Hydroflumethiazide | 33 gms. | 66 gms. | 33 gms. | 99 gms. |
| Bendroflumethiazide | 43 gms. | 86 gms. | 43 gms. | 129 gms. |
| Polythiazide | 44 gms. | 88 gms. | 44 gms. | 132 gms. |
| Methyclothiazide | 36 gms. | 72 gms. | 36 gms. | 108 gms. |
| Trichlormethiazide | 38 gms. | 76 gms. | 38 gms. | 114 gms. |
| Cyclothiazide | 39 gms. | 78 gms. | 39 gms. | 117 gms. |
| Cyclopenthiazide | 38 gms. | 76 gms. | 38 gms. | 114 gms. |

The ratio of thiazide compound to anion-exchange resin, to cation exchange resin is that for each part by weight of the thiazide compound, two parts by weight of the anion exchange resin and one part by weight of the cation exchange resin. The remainder of the steps are the same as described above. The formed selected thiazide resin adsorbate complex obtained is formulated into unit dosage forms, each containing a sufficient amount of the selected resin thiazide compound to provide a hypertensive effect dissociated from diuresis, as described in Example 1 above. The particular unit dosage form is administered in from 4 to 8 consecutive hourly doses, once or twice daily.

The colloidal dispersion of the appropriate thiazide compound as prepared and used as described above, is preferably prepared at a pH of between pH 3 and pH 4 but this is not a critical parameter and both lower, more acidic pH values as well as the higher alkaline values may be used. Even the soluble metal salt of the selected thiazide compound may be used directly to form the solution to conduct the reaction with the described ion exchange resins. However, the comparative purity of the final product will be reduced. Although the integrity of the lipid-soluble, free acid thiazide is enhanced in acid media, a corresponding lesser protective effect against the polarizing action of the gastric contents will occur when the formation of the resin adsorbate thiazide complex is carried out in strong acid solution.

EXAMPLE 3

Preparation of Hydroxy Metal Thiazide Salts

To an aqueous solution of hydrochlorothiazide prepared by dissolving 3 gms. of hydrochlorothiazide in 50 ml. of water containing 0.4 gms. of sodium hydroxide, 1.65 gms. of finely-powdered, aluminum hydroxychloride, $A_2(OH)_5C$, are added. The mixture is stirred until the pH of the reaction medium reaches approximately pH 7.2, and the solution becomes milky as the insoluble aluminum dihydroxy hydrochlorothiazide forms. The compound is white, amorphous powder, insoluble in water and is mildly alkaline in reaction containing about 70% by weight of hydrochlorothiazide.

In place of the hydrochlorothiazide described above, there may be substituted any of the thiazide compounds described in Example 1 above, and in the amount set forth below, the remainder of the steps being the same. The isolated compound is the formed salt, aluminum hydroxide salt, $A(OH)_2R$, wherein R is the selected thiazide compound from the group set forth below:

| Thiazide Compound | Weight Of Thiazide Compound | Weight of $Al_2(OH)_5Cl$ |
|---|---|---|
| Bendroflumethiazide | 4.3 gm. | 1.8 gm. |
| Benzthiazide | 4.3 gm. | 1.8 gm. |
| Chlorothiazide | 3.0 gm. | 1.8 gm. |
| Cyclopenthiazide | 3.8 gm. | 1.8 gm. |
| Cyclothiazide | 3.9 gm. | 1.8 gm. |
| Flumethiazide | 3.3 gm. | 1.8 gm. |
| Hydroflumethiazide | 3.3 gm. | 1.8 gm. |
| Methyclothiazide | 3.6 gm. | 1.8 gm. |
| Polythiazide | 4.4 gm. | 1.8 gm. |
| Trichlormethiazide | 3.8 gm. | 1.8 gm. |

The aqueous solution of the reactant thiazide compound may be prepared directly with the sodium salt of the selected thiazide or an equivalent quantity of a soluble metal salt of the respective thiazide. The remainder of the steps being the same, the formed aluminum hydroxy thiazide compound isolated will be the same as that obtained by the methods described above.

The aluminum hydroxy thiazide compound is formulated into unit dosage forms containing an amount of the aluminum hydroxy thiazide salt to provide a sufficient quantity of the selected thiazide to achieve an antihypertensive effect dissociated from diuresis, when administered in from 4 to 8 consecutive hourly doses, once or twice daily.

EXAMPLE 4

When it is desired to use the loosly bonded combination of the appropriate thiazide compound with an insoluble metal hydroxide or metal carbonate compound to form a weak salt of the thiazide to protect the lipid soluble thiazide form against the polarizing effects of physiologic materials, then a metal hydroxide or carbonate compound selected from the group consisting of aluminum hydroxide, calcium hydroxid, calcium carbonate, magnesium hydroxide and magnesium carbonate is reacted with the appropriate thiazide compound to form a metallic oxy-salt of the selected thiazide compound.

A 1 gm. molar equivalent weight of the selected thiazide compound is combined with 1.1 gm. molecular weight of the particular metal hydroxider carbonate compound used from the group described above. The powders are intimately mixed and sufficient water added to just wet the mass which is then granulated through a No. 60 standard mesh screen and dried. The dried granulate is then used to prepare a unit dosage form which contains a sufficient amount of thiazide compound content which will provide an antihypertensive action dissociated from diuresis, as described in Example 1 above for the particular thiazide compound, particularly when administered of in from 4 to 8 consecutive hourly doses, once or twice daily.

EXAMPLE 5

The Preparation Of Thiazide Edetate Salts

To a solution of 3.75 gm. calcium disodium edetate dissolved in 50 ml. of distilled water is added 3.8 gm. of cyclopenthiazide and the mixture stirred until the cyclopenthiazide dissolves. The solvent is evaporated and the formed calcium disodium cyclopenthiazide recovered and dried.

In a similar manner other calcium disodium thiazide edetate salts may be prepared by substituting for the cyclopenthiazide, an appropriate quantity of a thiazide compound selected from the group listed below. The remainder of the steps being the same, the corresponding calcium disodium thiazide edetate salt will be obtained.

In place of the calcium disodium edetate as used above, there may be substituted an equimolar amount of the disodium salt of ethylene diamine tetracetic acid. The remainder of the steps being the same, the corresponding disodium thiazide edetate salt is obtained.

| Thiazide Compound | Weight of Thiazide Compound | Weight of Calcium Disodium Edetate | Weight of Disodium Edetate |
| --- | --- | --- | --- |
| Bendroflumethiazide | 43 gm. | 37.5 gm. | 33.6 gm. |
| Benzthiazide | 43 gm. | 37.5 gm. | 33.6 gm. |
| Chlorothiazide | 30 gm. | 37.5 gm. | 33.6 gm. |
| Cyclothiazide | 39 gm. | 37.5 gm. | 33.6 gm. |
| Flumethiazide | 33 gm. | 37.5 gm. | 33.6 gm. |
| Hydrochlorothiazide | 30 gm. | 37.5 gm. | 33.6 gm. |
| Hydroflumethiazide | 33 gm. | 37.5 gm. | 33.6 gm. |
| Methylclothiazide | 36 gm. | 37.5 gm. | 33.6 gm. |
| Polythiazide | 44 gm. | 37.5 gm. | 33.6 gm. |
| Trichlormethiazide | 38 gm. | 37.5 gm. | 33.6 gm. |

When the thiazide edetate salts are used to formulate unit dosage forms, then each unit dosage form will contain a sufficient quantity of the selected thiazide edetate salt, to provide an amount of the selected thiazide compound sufficient to cause an antihypertensive action dissociated from diuresis, when administered in from 4 to 8 consecutive hourly doses, once or twice daily, as described in Example 1, above.

EXAMPLE 6

When it is desired to prepare a hydrogen bonded molecular complex of a cellulose polymer and a thiazide compound described in Example 1 above, then one part by weight of the appropriate thiazide compound is reacted with an equal part by weight of a cellulose polymer such as hydroxyethylcellulose, hydroxymethylcellulose, hydroxypropylcellulose, carboxymethylcellulose and sodium carboxymethylcellulose.

An aqueous dispersion of the selected cellulose polymer is prepared, warmed to 50° C. and an equal part by weight of the selected thiazide compound added while stirring. When a uniform dispersion results, the mixture is set aside overnight and the solvent removed under vacuum. The resulting formed cellulose-thiazide molecular complex contains about 50% by weight of the selected thiazide compound and may be formulated into unit dosage forms for use in therapy.

Each unit dosage form is prepared with a sufficient amount of the cellulose thiazide molecular complex to provide a quantity of the thiazide compound to cause an antihypertensive action dissociated from diuresis as described in Example 1 above, when administered in from 4 to 8 consecutive hourly doses, once or twice daily.

EXAMPLE 7

To an aqueous solution containing 22 gms. of polyvinylpyrrolidone in 150 ml. of water is added 4.4 gms. of polythiazide and the mixture stirred while warming to 50° C. for one hour. The solvent is removed under vacuum and a glassy, colorless solid is obtained, which is the polyvinylpyrrolidone-polythiazide complex. The polyvinylpyrrolidone-polythiazide molecular complex is soluble in water and may be used directly in therapy, or formulated into unit dosage forms.

In place of the polythiazide described above, there may be substituted any other of the thiazide compounds described in Example 1 above, in an equivalent molar amount so that the ratio in parts by weight is 2 gm. of the selected thiazide compound or 1:5 for each 10 gm. of polyvinylpyrrolidone used. The formed polyvinylpyrrolidone thiazide molecular complex is water-soluble and may be used directly in therapy, or formulated into dosage forms as described above.

Each unit dosage form contains a sufficient quantity of the selected polyvinylpyrrolidone-thiazide molecular complex to provide the appropriate amount of the particular thiazide, as described in Example 1 above, to achieve an antihypertensive action dissociated from diuresis, when administered in from 4 to 8 consecutive hourly doses, once or twice daily.

EXAMPLE 8

The Preparation Of The Beta-Adrenergic Receptor Blocking Amine Thiazide Salts To 50 ml. of a methanol solution containing 3 gm. of propanolol hydrochloride is slowly added 3.2 gm. of sodium hydrochlorothiazide dissolved in 50 ml. of methanol. The mixture is warmed to about 50° C. for about ½ hour while stirring and the solvent concentrated to 1/3 its volume and filtered. The clear filtrate is poured into 200 ml. of ice water and the formed propanolol-hydrochlorothiazide salt recovered, dried and formulated into appropriate unit dosage forms.

In place of the propanolol hydrochloride described above, there may be substituted a hydrochloric acid salt of another beta-adrenergic blocking amine, such as alprenolol, butridine, butoxamine, dichlorisoproterenol, nifenalol, oxprenolol, practolol, pronethalol, propranolol, solatolol, toliprolol. The amount of the appropriate beta-blocking amine reagent used is about 1.5 gm. molar equivalent weights for each part by weight of the hydrochlorothiazide used. Thus, to prepare a 0.01 molar equivalent weight of the appropriate amine, hydrochlorothiazide salt, then between 4.0 and 4.5 gm. of the selected amine reactant is used for each 3.2 gm. of sodium hydrochlorothiazide. The remainder of the steps are the same and the appropriate amine hydrochlorothiazide salt is obtained in high yield.

In place of the sodium hydrochlorothiazide described above, there may be substituted an equivalent molar amount of a sodium thiazide compound described in Example 1 above. The remainder of the steps are the same and the appropriate propanolol thiazide salt is obtained in high yield.

In practice, the beta-adrenergic blocking amine thiazide salts, as described above, are administered as unit dose compositions, each unit dose containing a sufficient quantity of the appropriate amine thiazide salt to provide a thiazide dose of from 7% to 25% of the diuretic dose for the respective thiazide compound used, administered in from 4 to 8 consecutive hourly doses, once or twice daily to achieve an antihypertensive effect dissociated from diuresis.

EXAMPLE 9

Preparation Of Amiloride-Thiazide Salts

To a methanol solution containing 32.3 gm. of sodium hydrochlorothiazide dissolved in 100 ml. of methanol is added 40 gm. of amiloride hydrochloride-dihydrate,(3,5-Diamino-N-(aminoiminomethyl)6-chloropyrazine-carboxamide-hydrochloride, dihydrate), dissolved in 200 ml. of methanol. The mixture is warmed to 50° C. and filtered. The methanol solvent is concentrated to 1/3 its volume and the whole set aside to crystallize in an ice chest. The formed amiloride hydrochlorothiazide crystals are isolated and dried. The formed amiloride-hydrochlorothiazide salt is a white crystalline solid, melting above 260° C. with decomposition.

In place of the sodium hydrochlorothiazide described above, there may be substituted in a gram molar equivalent quantity a sodium thiazide compound selected from the group described in Example 1 above and set forth below. The amount of the reagent required to form the amiloride-corresponding thiazide salt is:

| Thiazide Compound | Weight Of Sodium Thiazide Compound | Weight Of Amiloride HCl.2H$_2$O |
|---|---|---|
| Bendroflumethiazide | 45.3 gm. | 45.0 gm. |
| Benzthiazide | 46.3 gm. | 45.0 gm. |
| Chlorothiazide | 32.3 gm. | 45.0 gm. |
| Cyclopenthiazide | 40.3 gm. | 45.0 gm. |
| Cyclothiazide | 41.3 gm. | 45.0 gm. |
| Flumethiazide | 35.3 gm. | 45.0 gm. |
| Hydroflumethiazide | 35.3 gm. | 45.0 gm. |
| Methyclothiazide | 38.3 gm. | 45.0 gm. |
| Polythiazide | 46.3 gm. | 45.0 gm. |
| Trichlormethiazide | 40.3 gm. | 45.0 gm. |

The remainder of the steps are the same and the formed amiloride thiazide salt is obtained as a white crystalline solid in yields better than 90% of theory.

In practice the preferred amiloride thiazide salt is administered as a pharmaceutical unit dose composition containing a sufficient quantity of the amiloride thiazide salt to provide from 7% to 15% by weight of the diuretic dose of the selected thiazide moiety. The pharmaceutical unit dose composition is administered in from 4 to 8 consecutive hourly doses, once or twice daily, to achieve the desired antihypertensive vasomotor effect without diuresis.

While the invention has been described with respect to particular compounds and dosages, it is apparent that variations and modifications of the invention can be made without departing from the spirit or scope thereof.

What is claimed is:

1. Method of effecting antihypertensive action without diureses which comprises administering to a patient requiring antihypertensive effect but in whom diureses is not desired a pharmaceutically acceptable thiazide diuretic having a predetermined diuretic effective dose, the amount of said thiazide diuretic administered being sufficient to achieve antihypertension while being insufficient to achieve effective diuresis.

2. Method according to claim 1 wherein the amount of said thiazide diuretic administered is 7-25% of the diuretic effective dose.

3. Method according to claim 1 wherein said thiazide is administered 4-8 times at hourly intervals 1-2 times per day.

4. Method according to claim 3 wherein the amount administered each time is 7-25% of the diuretic effective dose.

5. Method according to claim 1 wherein said thiazide diuretic is selected from the group consisting of chlorothiazide, flumethiazide, benzthiazide, hydrochlorothiazide, hydroflumethiazide, bendroflumethiazide, polythiazide, methycyclothiazide, trichlormethiazide, cyclothiazide and cyclopenthiazide.

6. Method according to claim 5 wherein the amount of the thiazide administered is 7-25% of the diuretic effective dose.

7. Method according to claim 5 wherein said thiazide is administered 4-8 times at hourly intervals 1-2 times per day.

8. Method according to claim 7 wherein the amount administered each time is 7-25% of the diuretic effective dose.

9. Method of effecting diuretic action in a patient requiring the same, which comprises administering to such patient a diuretic effective dose of a complex of a pharmaceutically acceptable thiazide diuretic and a pharmaceutically acceptable mixed cation-anion exchange resin.

10. Method of effecting antihypertensive action in a patient requiring the same which comprises administering to such patient an antihypertensive effective dose of a complex of pharmaceutically acceptable thiazide diuretic and a pharmaceutically acceptable mixed cation-anion exchange resin.

11. Method of effecting antihypertensive action without diuresis in a patient requiring antihypertensive effect without diuresis which comprises administering to such patient a complex of a pharmaceutically acceptable thiazide diuretic and a pharmaceutically acceptable mixed cation-anion exchange resin in a dose which is sufficient to achieve antihypertension while being insufficient to achieve effective diuresis.

12. Method of effecting diuretic action in a patient requiring the same which comprises administering to such patient a diuretic effective amount of an insoluble basic hydroxymetalthiazide salt of a pharmaceutically acceptable thiazide diuretic and a pharmaceutically acceptable metal hydroxyl compound.

13. Method according to claim 12 wherein said metal is aluminum, calcium or magnesium.

14. Method of effecting antihypertensive action without diuresis in a patient requiring antihypertensive effect without diuresis which comprises administering to such patient an insoluble basic hydroxymetalthiazide salt of a pharmaceutically acceptable thiazide diuretic and a pharmaceutically acceptable metal hydroxyl compound in an amount sufficient to achieve antihypertension while being insufficient to achieve effective diuresis.

15. Method according to claim 14 wherein said metal is aluminum, calcium or magnesium.

16. Method of effecting diuretic action in a patient requiring the same which comprises administering to such patient a diuretic effective amount of a salt of a pharmaceutically acceptable thiazide diuretic and calcium disodium edetate or disodium edetate.

17. Method of effecting antihypertensive action in a patient requiring the same which comprises administering to such patient an antihypertensive effective amount of a salt of a pharmaceutically acceptable thiazide diuretic and calcium disodium edetate or disodium edetate.

18. Method of effecting antihypertensive action without diuresis, which comprises administering to a patient requiring antihypertension without diuresis a salt of a pharmaceutically acceptable thiazide diuretic and calcium disodium edetate or disodium edetate in an amount sufficient to achieve antihypertension while being insufficient to achieve effective diuresis.

19. Method of effecting diuretic action in a patient requiring the same which comprises administering to such patient a diuretic effective amount of a thiazide composition wherein the thiazide is protected in the gastrointestinal tract, said composition comprising a thiazide diuretic and calcium disodium edetate or disodium edetate.

20. Method of effecting antihypertensive action in a patient requiring the same which comprises administering to such patient a diuretic effective amount of a thiazide composition wherein the thiazide is protected in the gastrointestinal tract, said composition comprising a thiazide diuretic and calcium disodium edetate or disodium edetate.

21. Method of effecting antihypertensive action without diuresis which comprises administering to a patient requiring antihypertensive effect without diuresis a thiazide composition wherein the thiazide is protected in the gastrointestinal tract, said composition comprising a thiazide diuretic and calcium disodium edetate or disodium edetate in an amount sufficient to achieve antihypertension while being insufficient to achieve effective diuresis.

22. Method of effecting diuretic action in a patient requiring the same which comprises administering to such patient a diuretic effective amount of a molecular complex of a pharmaceutically acceptable thiazide diuretic and a long chain polymer selected from the group consisting of hydroxy alkyl cellulose polymers, carboxy methyl cellulose and polyvinylpyrrolidone.

23. Method of effecting antihypertensive action in a patient requiring the same which comprises administering to such patient an antihypertensive effective amount of a molecular complex of a pharmaceutically acceptable thiazide diuretic and a long chain polymer selected from the group consisting of hydroxy alkyl cellulose polymers, carboxy methyl cellulose and polyvinylpyrrolidone.

24. Method of effecting antihypertensive action without diuresis which comprises administering to a patient requiring antihypertensive effect without diuresis a molecular complex of a pharmaceutically acceptable thiazide diuretic and a long chain polymer selected from the group consisting of hydrdoxy alkyl cellulose polymers, carboxy methyl cellulose and polyvinylpyrrolidone in an amount sufficient to achieve antihypertension while being insufficient to achieve effective diuresis.

25. Method of effecting antihypertensive action without diuresis which comprises administering to a patient requiring antihypertensive effect without diuresis a composition having augmented antihypertensive action, said composition comprising an antihypertensive effective amount of a pharmaceutically acceptable thiazide diuretic and an effective amount of a beta-adrenergic blocking amine in an amount sufficient to effect antihypertensive action while being insufficient to achieve effective diuresis.

26. Method according to claim 25 wherein said thiazide diuretic is selected from the group consisting of chlorothizide, flumethizide, benzthiazide, hydrochlorothiazide, hydroflumethiazide, bendroflumethiazide, polythiazide, methcyclothiazide, trichlormethiazide, cyclothiaizde and cyclopenthiazide.

27. Method according to claim 26 wherein said beta-adrenergic blocking amine is alprenolol, butidrine, butoxamine, dichlorisoproterenol, nifenalol, oxyprenolol, practolol, pronethalol, propanolol, satalol or toliprolol.

28. Method of effecting antihypertensive action without diuresis which comprises administering to a patient requiring antihypertensive effect without diuresis a compound of a pharmaceutically acceptable thiazide and a beta-adrenergic blocking amine wherein said thiazide is selected from the group consisting of chlorothiazide, flumethiazide, benzthiazide, hydrochlorothiazide, hydroflumethiazide, bendroflumethiazide, polythiazide, methcyclothiazide, trichlormethiazide, cyclothiazide and cyclopenthiazide in an amount insufficient to effect antihypertensive action while being sufficient to achieve effective diuresis.

29. Method of effecting antihypertensive action without diuresis which comprises administering to a patient requiring antihypertensive effect without diuresis a salt of amiloride and a pharmaceutically acceptable thiazide diuretic in an amount sufficient to effect antihypertensive action while being insufficient to achieve effective diuresis.

30. Method according to claim 29 wherein said thiazide is selected from the group consisting of chlorothiazide, flumethiazide, benzthiazide, hydrochlorothiazide, hydroflumethiazide, bendroflumethiazide, polythiazide, methcyclothiazide, trichlormethiazide, cyclothiazide and cyclopenthiazide.

* * * * *